July 8, 1947. M. KROWKA Plant Pat. 743
ROSE PLANT
Filed May 31, 1946
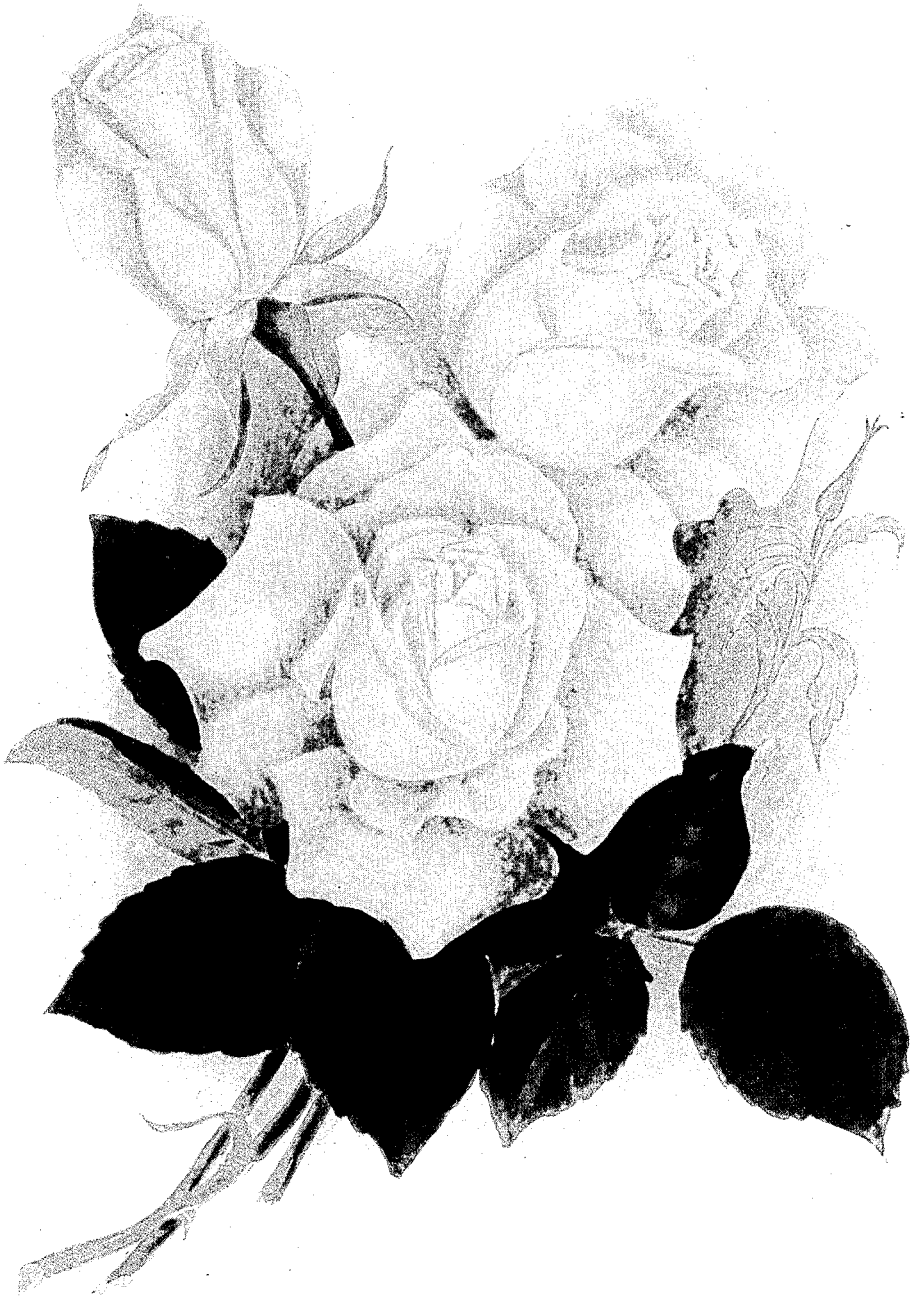
WITNESS
Addison E. Avery
INVENTOR,
MICHAEL KROWKA,
by Rummler Rummler & Davis,
ATTYS.

Patented July 8, 1947

UNITED STATES PATENT OFFICE

743

ROSE PLANT

Michael Krowka, Des Plaines, Ill., assignor to M & J Krowka, Des Plaines, Ill., a partnership composed of Michael and Joseph Krowka Application May 31, 1946, Serial No. 673,247

1 Claim. (Cl. 47—61)

This new variety of rose plant herein described and illustrated is a sport of the well-known variety of rose known as "Better Times" (Plant Pat. 23). In and since the year 1942 this sport plant has been asexually reproduced by numerous budding operations, and its novel characteristics have come true to form and are established.

The new variety is distinguishable from the parent plant mainly in the darker red tones of the flowers, longer tapering buds, and darker blue-green foliage. The new plant grows vigorously, blossoms freely and continuously, the blooms being recurrent approximately every eight weeks, has a good resistance to the diseases prevalent among rose plants, and the cut flowers have long-lasting qualities. The inner surface of the petals has a velvet-like texture that produces rich shadings as the light falls on the varying surface curvatures and the outer surface of the petals has a satin-like luster, both of these features contributing to the beauty of the shading in the deep pockets between petals. The petals are also slightly translucent and this also adds richness to the coloring. The petals are wide with wavy outer edges that curl backward gracefully along chordal lines. The outer petals are 2¾ inches long and 2¾ inches wide.

The petals do not fall off. The blooms hold their color persistently and have no undesirable fading reaction. Unlike other known varieties of red roses, it does not have a fading reaction of the usual bluish tinge. On the contrary, it appears to become a deeper red.

The accompanying painting shows in full color specimens of this new variety in various stages of development.

This new variety in plant structure and good habits is similar to the parent plant "Better Times," but it differs markedly in the brilliant deep red coloring of the bloom which shades almost to black where the surface is in shadow and displays varying rich shades of red, according to the angle at which the light strikes the surface of the petals. The bloom retains its color persistently and does not have the tendency to dark bluish fading that is common to red rose varieties.

Although the bloom bud is longer than that of its parent, it is compact with long sepals hooding the petals until it begins to open; and has the breadth and depth of the full-blown flower with large petals and the compact, high center. The flower stems are strong, sturdy, and practically thornless, except near the main stem. The foliage is smooth and of an attractive blue-green color, sufficient in quantity to form a background contrast for the blooms. In the fully open bloom the central group of petals stand out prominently and solid even in the final stage, consistently hooding the stigmas.

The following is a detailed description of the new variety:

*Flower*

Blooming habit: Recurrent—every 8 weeks.

Bud:

*Size.*—Approximately 2 inches long, tightly furled.

*Sepals.*—5, long and sharply pointed.

Bloom:

*Size.*—4½ to 5 inches in diameter x 2¾ inches in depth. Single outer petal, 2¾ inches x 2¾ inches deep.

*Borne.*—Singly.

*Petalage.*—25 to 30.

*Color.*—Darker red than "Better Times."

*Appearance.*—Inside, velvety; outside, satiny.

*Discoloration.*—Not discernible.

*Texture.*—Velvety, substantial.

*Affected by wet or hot weather.*—No.

*Persistence (hang on and dry).*—Long-lasting.

*Fragrance.*—Average rose scent.

*Disease resistance.*—Good.

*Plant*

Form: Bush.

*Height.*—5 to 5½ feet.

Foliage:

*Color.*—Darker than "Better Times"—dark Blue-Green.

*Size.*—Approximately 3½ inches long x 2 inches wide.

*Texture.*—Smooth, leathery. Shape—oblate, pointed.

*Thorns.*—A couple toward base of stem.

The color designations according to Robert Ridgway's Color Standards and Nomenclature are as follows:

| Part | Plate |
|---|---|
| Lightest portion of main body color, "Pomegranate Purple" | XII |
| Shading into large areas of "Rose Red" | XII |
| In certain light, dark sheen appears "Bordeaux" minus | XII |
| Back, or outside of petals, "Tyrian Rose" | XII |
| Main leaf—green—"Dusky Olive Green" | XLI |
| Back of leaf, "Andover Green" | XLVII |
| Calyx, "Scheele's Green" | VI |
| Stem, "Scheele's Green" | VI |
| Inside calyx, "Mytho Green" | XLI |

Among the dominant features of this new variety is its perfection in holding its rich dark red coloring to its final stage and the perfection of its buds at all stages of cutting. This enables the rose to be cut in the bud form and consequently to be in excellent condition for shipping and rehandling.

Having thus disclosed the invention, I claim:

A new and distinct variety of rose plant, as herein shown and described, characterized particularly by the unique rich deep red color of its flowers; the long, pointed compact buds; the shape and size of the blooms; the depth of the compact central area of the flowers; and the long-lasting resistance to fading of its petals.

MICHAEL KROWKA.